(12) United States Patent
Kadogawa et al.

(10) Patent No.: US 7,057,792 B2
(45) Date of Patent: Jun. 6, 2006

(54) OPTICAL SENSOR UNIT FOR MEASURING CURRENT AND VOLTAGE OF HIGH FREQUENCY

(75) Inventors: Yutaka Kadogawa, Miyazaki (JP); Naoji Moriya, Kyoto (JP); Toshinori Tsuji, Miyazaki (JP)

(73) Assignees: Oki Electric Industry Co., Ltd., Tokyo (JP); Miyazaki Oki Electric Co., Ltd., Miyazaki (JP); Shimadzu Corporation, Kyoto (JP); Tadamitsu Kaneko, Miyazaki (JP)

( * ) Notice: Subject to any disclaimer, the term of this patent is extended or adjusted under 35 U.S.C. 154(b) by 358 days.

(21) Appl. No.: 10/459,549

(22) Filed: Jun. 12, 2003

(65) Prior Publication Data

US 2004/0041083 A1   Mar. 4, 2004

(30) Foreign Application Priority Data

Aug. 30, 2002   (JP) .............................. 2002-252902

(51) Int. Cl.
*G02F 1/09* (2006.01)
*G02F 1/03* (2006.01)
*G02F 1/01* (2006.01)
*G01R 31/00* (2006.01)
*G01R 33/02* (2006.01)

(52) U.S. Cl. ...................... 359/281; 359/280; 359/257; 324/96; 324/244.1; 250/225

(58) Field of Classification Search ................ 359/280, 359/281, 257, 322, 324, 484; 324/96, 144, 324/244.1, 260; 250/214.1, 225
See application file for complete search history.

(56) References Cited

U.S. PATENT DOCUMENTS

| | | | |
|---|---|---|---|
| 3,983,477 A * | 9/1976 | Stuchly et al. .......... 324/117 R |
| 4,232,264 A * | 11/1980 | Papp et al. .................... 324/96 |
| 4,253,061 A * | 2/1981 | Ono et al. ..................... 324/96 |
| 4,731,581 A * | 3/1988 | Doriath et al. ........... 324/244.1 |
| 4,933,629 A * | 6/1990 | Kozuka et al. ................ 324/96 |
| 5,134,361 A * | 7/1992 | Pillow ......................... 324/96 |
| 5,477,134 A | 12/1995 | Hamada ...................... 324/96 |
| 5,635,829 A | 6/1997 | Hamada ...................... 324/96 |
| 5,736,856 A * | 4/1998 | Oliver et al. ............. 324/244.1 |
| 6,140,634 A | 10/2000 | Bosselmann ................ 250/225 |
| 6,312,556 B1 | 11/2001 | Donohoe et al. ....... 156/345.28 |
| 6,404,190 B1 * | 6/2002 | Itoh et al. ................. 324/244.1 |

FOREIGN PATENT DOCUMENTS

| JP | 6-52994 | 2/1994 |
|---|---|---|
| JP | 8-105919 | 4/1996 |
| JP | 2001-68459 | 3/2001 |

* cited by examiner

Primary Examiner—Loha Ben
(74) Attorney, Agent, or Firm—Wenderoth, Lind & Ponack, L.L.P.

(57) ABSTRACT

An optical sensor unit, free from electrical noise, includes a sensor case which has both lateral sides having high frequency connectors mounted thereon, and a metallic plate mounted inside the case. The metallic plate has both ends connected to inner conductors of the high frequency connectors, and its upper surface having a current and a voltage sensor unit mounted thereon for measuring the high frequency current and voltage, respectively. The current sensor unit includes total-reflection mirrors and a current sensor, and the voltage sensor unit includes further total-reflection mirrors and a voltage sensor. The voltage sensor has its upper surface having an electrode provided thereon to be connected to the sensor case. The laser light from outside is input to the current and voltage sensor units over optical fibers. The signal light output from the current and voltage sensor units is taken outside on output optical fibers.

11 Claims, 11 Drawing Sheets

OPTICAL SENSOR UNIT FOR MEASURING CURRENT AND VOLTAGE OF HIGH FREQUENCY

BACKGROUND OF THE INVENTION

1. Field of the Invention

The present invention relates to an optical sensor unit for measuring the current and the voltage of a high frequency transmitted over e.g., a coaxial cable.

2. Description of the Background Art

In a semiconductor manufacturing system, employing high frequency plasma, the fundamental and harmonics components of a high frequency of, e.g. 400 kHz or 13.56 MHz, supplied from a high frequency power supply on a coaxial cable to a vacuum processing chamber are calculated by harmonics measuring equipment to oversee the manufacturing process. In conventional harmonics measuring equipment, a sensor unit comprised of a high-frequency measuring circuit including inductors and capacitors electrically senses the current and the voltage of the high frequency applied to the vacuum processing chamber, and transmits signals representative of the current and the voltage thus sensed on shielded signal cables to a data processor system, which analyzes the waveform by fast Fourier transform (FFT) to determine the current, voltage and the phase difference of the fundamental and second to fifth harmonics components, as disclosed for example in the Japanese laid-open publication Nos. 52994/1994 and 2001-68459.

With the above-described harmonics measurement equipment, however, if the aforementioned sensor unit is introduced in the transmission line for transferring the high frequency supplied from the high frequency power source to the vacuum processing chamber, there may be occasions where the signal cables for taking out sensed signals, connected to the sensor unit, operate as antennas to render it difficult to establish matching between the high frequency power source and a plasma discharging device in the vacuum processing chamber. Moreover, although a common optical sensor for measuring the high frequency is disclosed in for example the Japanese laid-open publication No. 105919/1996, there lacks the disclosure of an optical sensor convenient for measuring the high frequency supplied from the high frequency power supply to the vacuum processing chamber.

SUMMARY OF THE INVENTION

It is an object of the present invention to overcome the above-depicted problems of the conventional technique and to provide an optical sensor unit, which does not harm the operation of the semiconductor manufacturing system.

For accomplishing the above object, the present invention provides an optical sensor unit comprising a transmission line for propagating a high frequency, a current sensor unit for converting first incident light into a first optical signal, intensity of which varies in response to a magnetic field of the high frequency, a voltage sensor unit for converting second incident light into a second optical signal, intensity of which varies in response to an electric field of the high frequency, an optical input unit for introducing from light provided from outside the first incident light to said current sensor unit and the second incident light to said voltage sensor unit.

The optical sensor unit may further comprise a first optical fiber for taking out the first optical signal to outside, and a second optical fiber for taking out the second optical signal to outside, said optical input unit comprising a third optical fiber for providing the light provided from outside to said current sensor unit, and a fourth optical fiber for providing the light from outside to said voltage sensor unit.

Preferably, the current sensor unit includes a polarizer for linearly polarizing the incident light from the third optical fiber to output linearly polarized light, a Faraday cell for rotating a plane of polarization of the linearly polarized light in response to the magnetic field of the high frequency, and an analyzer for converting the light output from the Faraday cell into the optical signal, intensity of which varies according to the rotation of a plane of polarization of the light output from the Faraday cell.

It is also noted that the voltage sensor unit includes a polarizer for linearly polarizing the incident light from the fourth optical fiber to output linearly polarized light, a Pockels cell for elliptically polarizing the linearly polarized light to output elliptically polarized light in response to the electric field of the high frequency, a quarter-wavelength plate for controlling polarization of the elliptically polarized light to output, when field strength within the Pockels cell is zero, circular polarized light, and an analyzer for converting the light output from the quarter-wavelength plate into an optical signal, intensity of which varies according to the polarization of the linearly polarized light.

With the optical sensor unit of the present invention, in which the high frequency current and voltage are measured, using the light, and the results measured are output in the form of optical signals, measurement may be made with high accuracy without being affected by electrical noises.

By applying the high frequency voltage to the voltage sensor in the optical sensor unit so that the inner electric field is substantially parallel to the transmitted light, it is possible to eliminate the effect of expansion or contraction of the voltage sensor element with respect to measured voltage changes. Moreover, by using optically transparent electrodes as the electrodes for applying the high frequency voltage, it is possible to simplify alignment of the optical axis of the laser beam and the components of the voltage sensor unit. By providing the optical connectors for connection to the optical fibers and by employing polarization plane holding fibers as the optical fibers for interconnecting the optical sensor unit to the light source, it is possible to diminish the signal deterioration due to bending.

The present invention also provides harmonics measuring equipment comprising a light source for generating laser light, an optical sensor unit including a current sensor unit for changing a plane of polarization of the laser light in response to a magnetic field of high frequency input from outside to generate a first optical signal, intensity of which varies in response to the magnetic field, and a voltage sensor unit for changing a plane of polarization of the laser light in response to electric field of the high frequency to generate a second optical signal, intensity of which varies in response to the electric field, a photosensitive device for converting the first and second optical signals into electrical signals, and a data processor for analyzing the electrical signals to calculate harmonics components of the high frequency.

By using the harmonics measurement equipment, employing the optical sensor unit in accordance with the present invention, for, e.g. a semiconductor manufacturing system, it is possible to detect variations in the device that would be impossible to detect on simply monitoring conventional process parameters.

BRIEF DESCRIPTION OF THE DRAWINGS

The objects and features of the present invention will become more apparent from consideration of the following detailed description taken in conjunction with the accompanying drawings in which.

DESCRIPTION OF THE PREFERRED EMBODIMENTS

Figure 2:
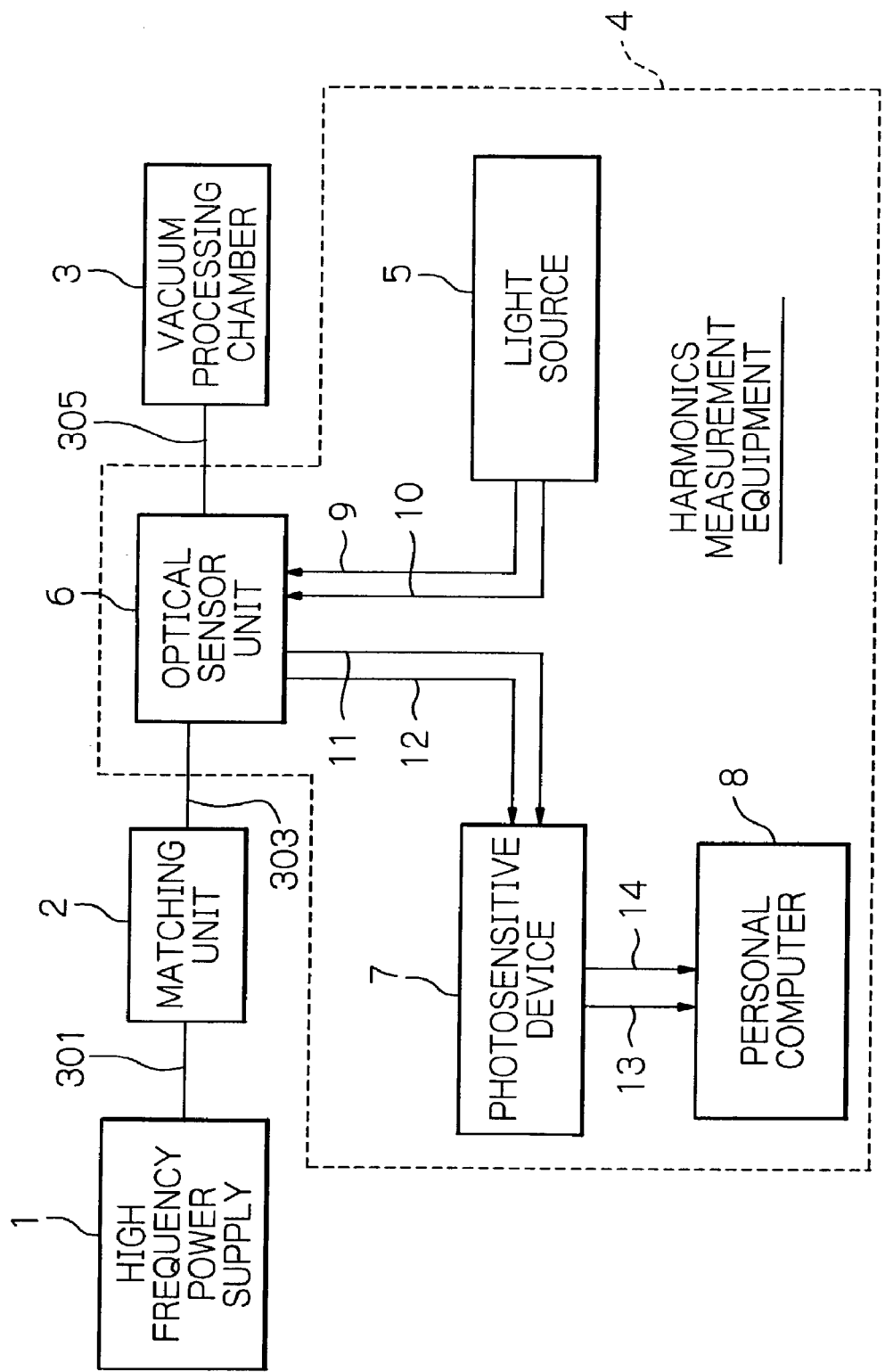
FIG. 2 is a schematic block diagram showing a semiconductor manufacturing system employing harmonics measurement equipment including an optical sensor unit in accordance with the present invention.

Referring to the accompanying drawings, preferred embodiments of the optical sensor unit in accordance with the present invention will be described. FIG. 2 shows a semiconductor manufacturing system comprising a high frequency power supply 1, a matching unit 2, a vacuum processing chamber 3, and a harmonics measurement equipment 4 interconnected as illustrated. The harmonics measurement equipment 4 includes a sensor unit 6 in accordance with the present invention. In FIG. 2, the high frequency, output from the high frequency power supply 1, is sent to the vacuum processing chamber 3 via the matching unit 2 and the harmonics measurement equipment 4. The harmonics measurement equipment 4 is adapted to measure the harmonics of the high frequency supplied to the vacuum processing chamber 3. Meanwhile, the high frequency power supply 1, matching unit 2, vacuum processing chamber 3 and harmonics measurement equipment 4 are interconnected by high frequency coaxial cables 301, 303 and 305 as illustrated. It is noted that the sensor unit 6 may be mounted within the matching unit 2, if so desired.

The harmonics measurement equipment 4 comprises a light source 5, the optical sensor unit 6, a photosensitive device 7 and a personal computer 8. The light source 5 and the optical sensor unit 6 are connected to each other by optical fibers 9 and 10. The optical sensor unit 6 and the photosensitive device 7 are connected to each other by optical fibers 11 and 12. The photosensitive device 7 and the personal computer 8 are connected by metallic wires 13 and 14. The light source 5 is e.g., a semiconductor laser emitting a stabilized laser beam with a wavelength of 1,310 nm. The laser light, output from the light source 5, is provided to the optical sensor unit 6 over optical fibers 9 and 10. For stabilizing the laser light output from the light source 5, a temperature compensation method or a DC monitor method, for example, may be used. In the following, signals are designated with reference numerals indicating lines on which the signals appear.

The optical sensor unit 6 includes a current sensor and a voltage sensor, not specifically illustrated in FIG. 2. The current sensor is adapted to adjust the plane of polarization of the laser light incident from the optical fiber 9 in response to the magnetic field of the high frequency 303 output from the matching unit 2, to generate an optical signal 11, the intensity of which is dependent upon the magnetic field of the high frequency. The voltage sensor is also adapted to change the plane of polarization of the light incident laser from the optical fiber 10 in response to the electric field of the high frequency 303 output from the matching unit 2, to generate another optical signal 12, the intensity of which depends upon the electric field of the high frequency. As stated above, the optical sensor unit 6 generates the optical signals 11 and 12 varying in intensity in response to the high frequency current and voltage, respectively.

The optical signals 11 and 12, generated in the optical sensor unit 6, are input to the photosensitive device 7 over the optical fibers 11 and 12. The photosensitive device 7 includes, for example, a photodiode, which is adapted to convert the optical signals 11 and 12 output from the optical sensor unit 6 to corresponding electrical signals to generate electrical signals varying in amplitude in response to the high frequency current and voltage, respectively. Meanwhile, the photosensitive device 7 has a frequency band width at least five times as broad as the fundamental frequency band of the high frequency being measured.

The electrical signals detected by the photosensitive device 7 are input to the personal computer 8 on signal wires 13 and 14. The personal computer 8 is a data processor system having frequency analysis means, such as Fourier transform function, and applies Fourier transform to the electrical signals 13 and 14 output from the photosensitive device 7 to calculate the fundamental and harmonics components of the high frequency current and voltage as well as the phase differences of the current and voltage for each of the fundamental and harmonics components. The so calculated results are used for overseeing the manufacturing process in the semiconductor manufacturing system.

Figure 1:
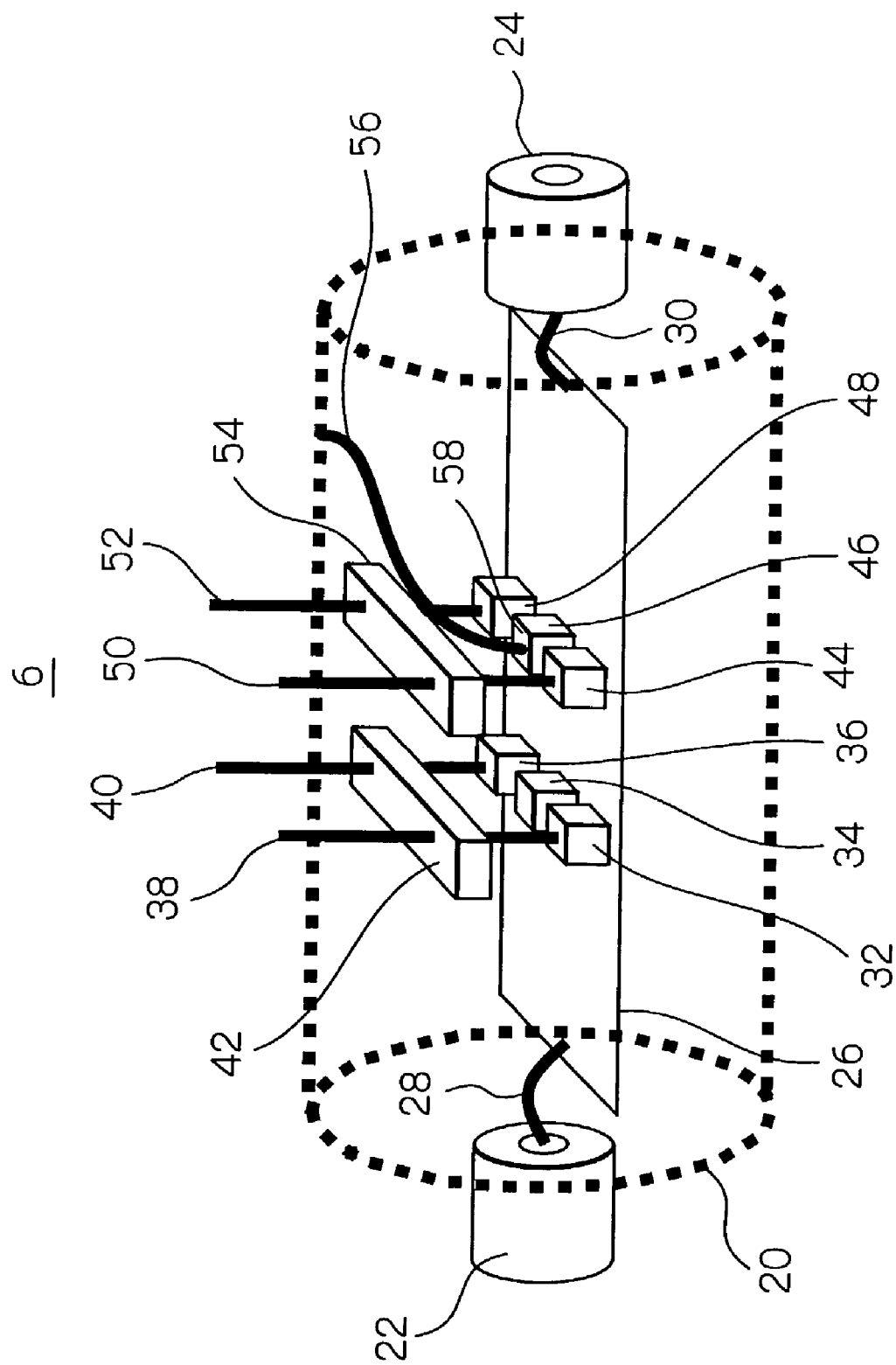
FIG. 1 is a schematic view showing a first embodiment of an optical sensor unit in accordance with the present invention.

FIG. 1 schematically shows a first embodiment of the optical sensor unit 6 in accordance with the present invention. The optical sensor unit 6 has a sensor case 20, which is a vessel formed of an electrically conductive material, such as metal, and housing therein, e.g. sensors. On both lateral sides of the sensor case 20 are mounted coaxial type high frequency connectors 22 and 24. With the use of the high frequency connectors 22 and 24, the optical sensor unit 6 can be connected to and disconnected from the high frequency cable lines 303 and 305 of the semiconductor manufacturing system. Since the shape of the high frequency connectors differs from one semiconductor manufacturing system to another, it is necessary to select the type of the high frequency connectors 22 and 24 appropriately for the particular semiconductor manufacturing system.

Within the sensor case 20, a plate-like conductor, such as a metallic board 26, is held in state of electrically isolated from the sensor case 20. The metallic plate 26 has its both ends connected to the inner conductors of the high frequency connectors 22 and 24 by wires 28 and 30, respectively. In this manner, the sensor case 20 and the metallic plate 26 form a transmission line for transmitting the high frequency, such that the high frequency input to the high frequency connector 22 is propagated to the high frequency connector 24 on a transmission path composed of the sensor case 20 and the metallic plate 26.

On the upper surface, or a primary surface, of the metallic plate 26, a total-reflection mirror 32, a current sensor 34 and another total-reflection mirror 36 are mounted at a preselected distance from each other on the same optical axis for forming the current sensor unit for measuring the high frequency current. An optical fiber 38 for providing the light to the total-reflection mirror 32 via a condenser lens, not shown, and an optical fiber 40 for receiving an optical signal output from the total-reflection mirror 36 are held at a position by an optical fiber mounting base 42 held to the sensor case 20.

Meanwhile, the optical fibers 38 and 40 correspond to the optical fibers 9 and 11 of FIG. 2, respectively. The light (laser beam) output from the light source 5 is provided to the total-reflection mirror 32 on the optical fiber 38, while the optical signal output from the total-reflection mirror 36 is provided to the photosensitive device 7 on the optical fiber 40.

With the illustrative embodiment, the optical fibers 38 and 50 are adapted to conduct respective, two optical beams emanating from the light source 5 to the associated current and voltage sensors. Alternatively, the system may be adapted to split a light beam emanating from the light source 5 into two optical beams to be conducted over the optical fibers 38 and 50 to the respective current and voltage sensors. To splitting the light beam, a beam splitter or an optical fiber type of optical coupler is advantageously applicable which has one input port and a couple of output ports.

On the upper surface of the metallic plate 26, a total-reflection mirror 44, a voltage sensor 46 and another total-reflection mirror 48 are mounted at a preselected distance from each other on the same optical axis and at a preselected distance from the current sensor unit for forming the voltage sensor unit for measuring the high frequency voltage. An optical fiber 50 for providing the light to the total-reflection mirror 44 via a condenser lens, not shown, and an optical fiber 52 for receiving an optical signal output from the total-reflection mirror 48, are held at a position by another optical fiber mounting base 54 mounted to the sensor case 20. On the upper surface, or primary surface, of the voltage sensor 46 is mounted an electrically conductive electrode 58 which is connected by a wire 56 to the sensor case 20. The metallic plate 26 and the electrode 58 operate as electrodes for applying a high frequency voltage to the voltage sensor 46 to generate an electric field therein.

The optical fibers 50 and 52 correspond to the optical fibers 10 and 12 of FIG. 2, respectively, such that the light (laser beam) output from the light source 5 is provided to the total-reflection mirror 44 over the optical fiber 50, while the optical signal output from the total-reflection mirror 48 is provided to the photosensitive device 7 over the optical cable 52.

In the present embodiment, the total-reflection mirrors 32, 36, 44 and 48 are used in order to align the mounting directions of the optical fibers 38, 40, 50 and 52 with respect to the sensor case 20. It is however possible to hold the optical fibers 38 and 50 so that the lights will be directly input to the current and voltage sensors 34 and 46 from the optical fibers 38 and 50 through the condenser lenses, respectively, and to hold the optical fibers 40 and 52 so that the optical signals output from the current and voltage sensors 34 and 46 will be directly received by the optical fibers 40 and 52, respectively, in which case the total-reflection mirrors 32, 36, 44 and 48 may be omitted.

The optical fibers 38, 40, 50 and 52 in the present embodiment, directly connected to the light source 5 or to the photosensitive device 7 of FIG. 2, may also be connected via an optical connector. In the case of the optical fiber 38, as an example, the portion lying above the mounting base 42 may be removed, an optical connector being secured to the optical fiber mounting base 42, one end of the remaining portion of the optical fiber 38 being then connected to the optical connector. The optical connector connected to the end the optical fiber 9 is inserted into the optical connector secured to the optical fiber mounting base 42. The same may be said of the optical fibers 40, 50 and 52, which may be connected as in the case of the optical fiber 38. However, by directly interconnecting the optical sensor unit 6, the light source 5 and the photosensitive device 7 by the optical fibers 38, 40, 50 and 52, it is possible to reduce the power loss of the light to a smaller value than in the case of connection via an optical connector.

Figure 3:
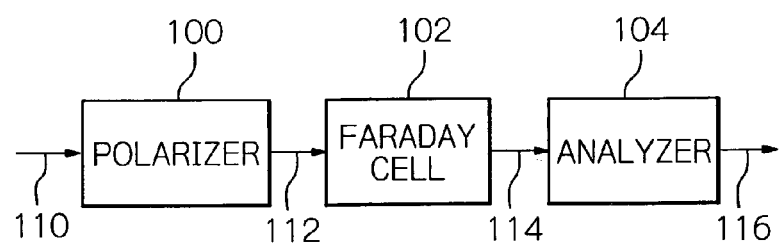
FIG. 3 is a schematic block diagram showing a current sensor included in the optical sensor unit of FIG. 1.

FIG. 3 is a schematic block diagram showing the current sensor 34. This current sensor 34 comprises a polarizer 100, a Faraday cell (RIG thin film) 102, and an analyzer 104 interconnected as depicted. Within the Faraday cell 102 is present a magnetic field, generated by the high frequency current flowing through the metallic plate 26, FIG. 1. To the polarizer 100 is provided the light 110 (laser beam) reflected by the total-reflection mirror 32, FIG. 1.

The polarizer 100 polarizes the light 110 incident into a linearly polarized light 112 to provide the light 112 to the Faraday cell 102. This Faraday cell 102, transmitting the linearly polarized light 112 therethrough, rotates its plane of polarization in response to the magnetic field generated by the high frequency current flowing through the metallic plane 26, FIG. 1, thereby generating light 114. The light 114 is provided to the analyzer 104. The analyzer 104 modulates the light 114 in intensity according to the rotation of the plane of polarization of the light 114 and outputs a so-modulated optical signal 116 to the total-reflection mirror 36, FIG. 1. The optical signal 116 is provided to the photosensitive device 7, FIG. 2, so as to be converted into electrical signals.

Figure 4:
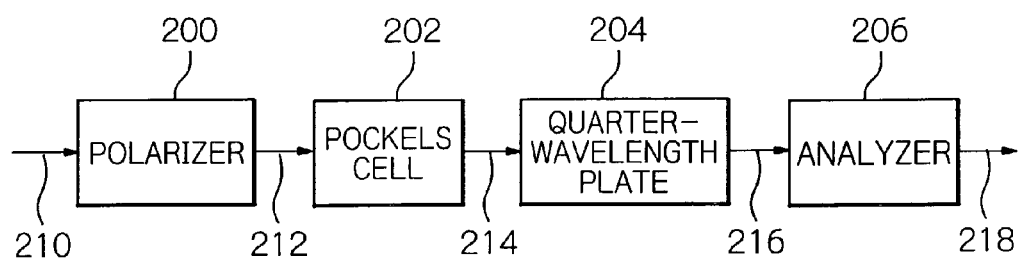
FIG. 4 is a schematic block diagram showing a voltage sensor included in the optical sensor unit of FIG. 1.

FIG. 4 is a schematic block diagram showing the voltage sensor 46. This voltage sensor 46 comprises a polarizer 200, a Pockels cell (BGO crystal) 202, a quarter-wavelength plate 204 and an analyzer 206 interconnected as shown. Within the Pockels cell 202 is present an electric field, exited by the high frequency voltage applied between the metallic plane 26 and the electrode 58, FIG. 1, in a direction at substantially right angle to the transmitted light beam. To the polarizer 200 is provided the light 210 (laser beam) reflected by the total-reflection mirror 44, FIG. 1.

The polarizer 200 linearly polarizes the incident light 210 and provides the thus polarized light 212 to the Pockels cell 202. The Pockels cell 202 elliptically polarizes the linearly polarized light 212 with the electric field generated therein to output linearly polarized light 214 to the quarter-wavelength plate 204. This quarter-wavelength plate 204 controls polarization of the incident light 214 so that, when the field strength within the Pockels cell 202 is zero, output light 216 will become the circular polarized light and provides the light 216 to the analyzer 206. The analyzer 206 modulates the light 216 in intensity with the electric field of the high frequency and outputs intensity-modulated optical signal 218 to the total-reflection mirror 48 of FIG. 1. This optical signal 218 is input to the photosensitive device 7, FIG. 2, so as to be converted into electrical signals.

Thus, with the optical sensor unit of the instant, first embodiment, in which the high frequency current and voltage are measured using the light and the measured results are output in the form of optical signals, the high frequency current and voltage can be measured with higher accuracy without being affected by electrical noises. By using the harmonics measurement equipment, including the optical sensor unit according to the present embodiment, as the semiconductor manufacturing system, it becomes possible to detect the variations of the system, which would not be detectable by simply monitoring the process parameters as conventionally.

Figure 5:
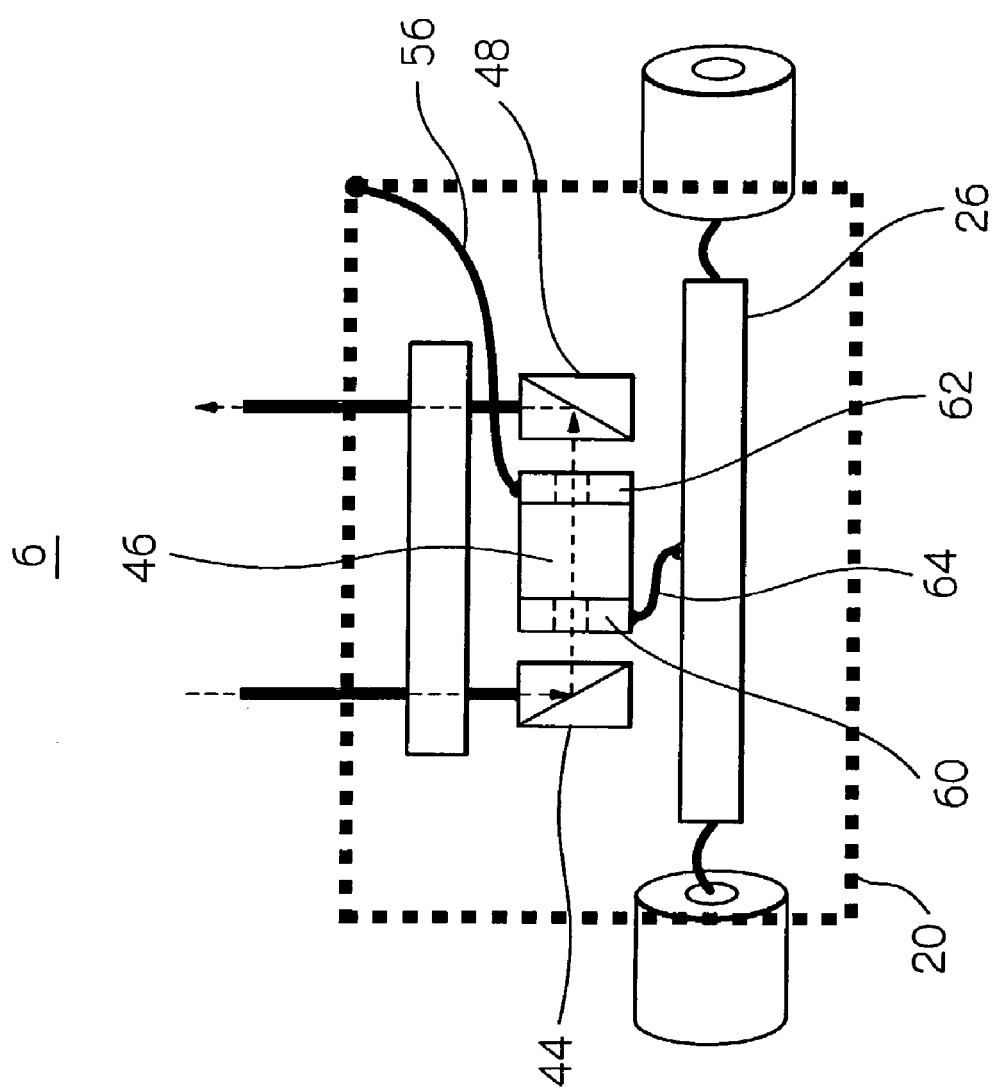
FIG. 5 is a schematic view showing a second embodiment of an optical sensor unit in accordance with the present invention.

FIG. 5 schematically shows a second, alternative embodiment of the optical sensor unit in accordance with the present invention. In the first embodiment, shown in FIG. 1, the electrode 58 is mounted so that the direction of the electric field present in the Pockels cell 202 of the voltage sensor 46 is at substantially right angles to the direction of the transmitted light. In the present, second embodiment, the electrodes 60 and 62 are mounted so that the direction of the electric field generated in the Pockels cell 202 of the voltage sensor 46 will be parallel to the direction of the transmitted light. The present second embodiment is the same as the first embodiment except this voltage sensor section.

In FIG. 5, the current sensor unit is omitted from the figure, with only the voltage sensor unit being shown and the parts or components corresponding to those shown in FIG. 1 are designated with the same reference numerals. The total-reflection mirror 44, voltage sensor 46 and the total-reflection mirror 48, forming the voltage sensor unit, are mounted at a spacing above the upper surface of the metallic plate 26 in the figure at a preselected interval on the same optical axis. For example, the voltage sensor unit may be secured on a non-electrically conductive spacer, not shown, affixed to the upper surface of the metallic plate 26. Meanwhile, it is sufficient for the voltage sensor 46 to be spaced apart from the metallic plate 26 to such an extent that the metallic plate 26 does not affect the internal electric field.

On both ends of the voltage sensor 46 where the light is input or output, there are provided metal electrodes 60 and 62 having through-holes for passage of light, for example, in the order of 2 mm in diameter. The electrode 60 is connected to the metallic plate 26 by a wire 64, while the electrode 62 is connected to the sensor case 20 via another connecting wire 56. This applies the voltage of the high frequency propagating on the metallic plate 26 between the electrodes 60 and 62, such that an electric field substantially parallel to the transmitted light is generated within the voltage sensor 46. It is noted that the electrodes 60 and 62 may be connected to the sensor case 20 and the metallic plate 26 by wiring connections, respectively.

If the direction of the electric field within the voltage sensor 46 is substantially orthogonal to that of the transmitted light, the voltage sensor 46 measures the voltage change which is proportionate to the optical path length and inversely proportionate to the distance between the electrodes. Thus, if the sensor element is subjected to marked expansion or contraction due to changes in the ambient temperature, the amount of voltage change is measured as varied. In the present embodiment, since the high frequency voltage is applied to the voltage sensor 46 so that the electric field within the voltage sensor 46 is substantially parallel to the transmitted light, the effect of the expansion or contraction of the voltage sensor 46 on the amount of variation of the voltage being measured is eliminated, thus assuring stabilized measurement.

Figure 6:
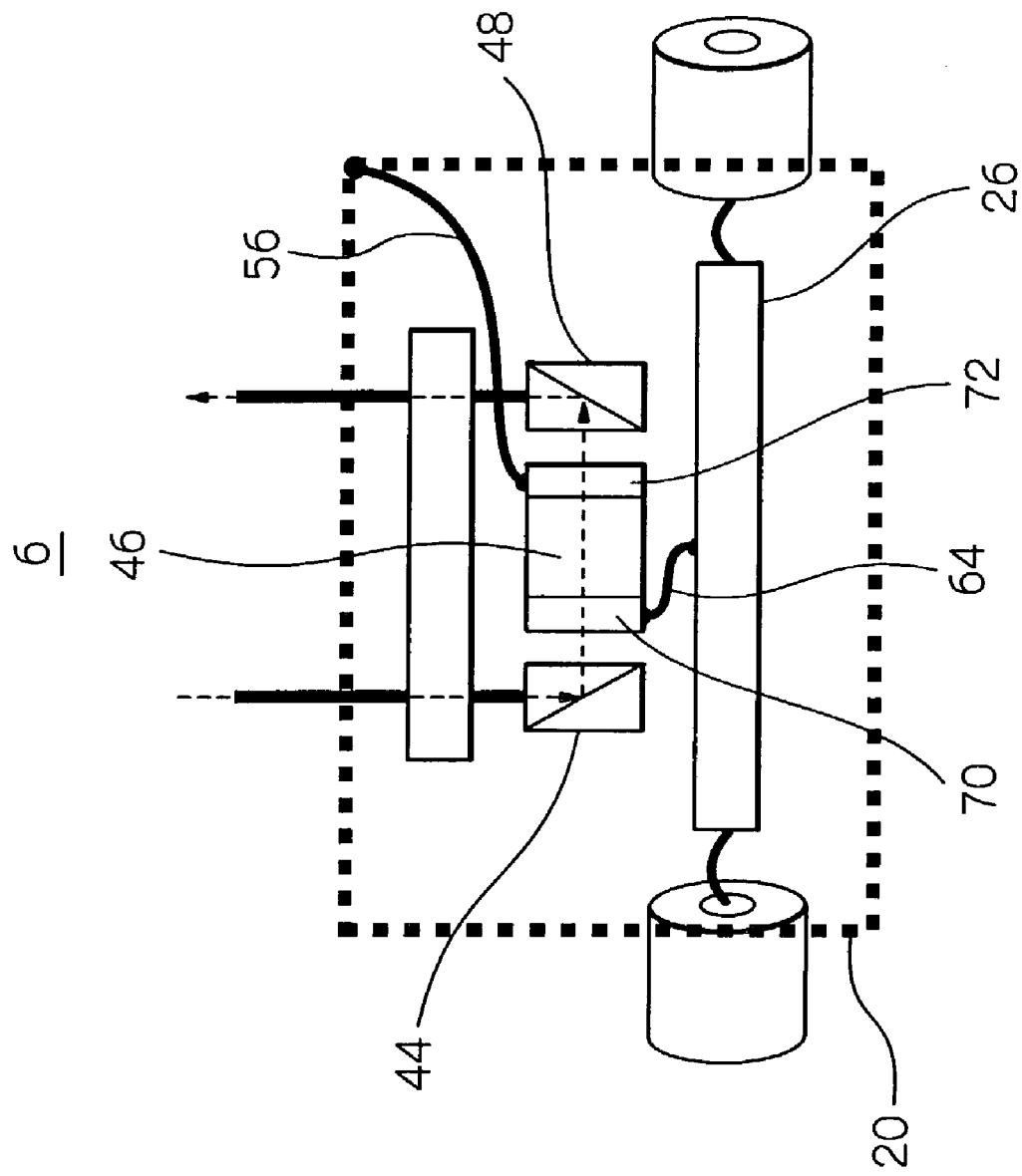
FIG. 6 is a schematic view showing a third embodiment of an optical sensor unit in accordance with the present invention.

FIG. 6 shows a third, further alternative embodiment of the optical sensor unit in accordance with the present invention. With the optical sensor unit 6 of FIG. 5, metal electrodes are used as the electrodes 60 and 62 of the voltage sensor 46, so that a through-hole for light transmission needs to be provided centrally of each electrode. In the present embodiment shown in FIG. 6, optically transparent electrodes 70 and 72 are used which are made of an electrically conductive material with low laser light absorption coefficients. These transparent electrodes 70 and 72 are fixed with an also optically transparent adhesive to both ends of the voltage sensor 46.

With this third embodiment, the alignment between the optical axis of the laser light and the voltage sensor element may be simpler than with the second embodiment, thus assuring facilitated mass production of the sensor. Moreover, by forming the transparent electrodes through the vapor deposition or CVD (chemical vapor deposition), the production process may be controlled to diminish variations in characteristics, such as absorptivity or reflectivity of the laser light, liable to be produced during the adhesion step.

Figure 7:
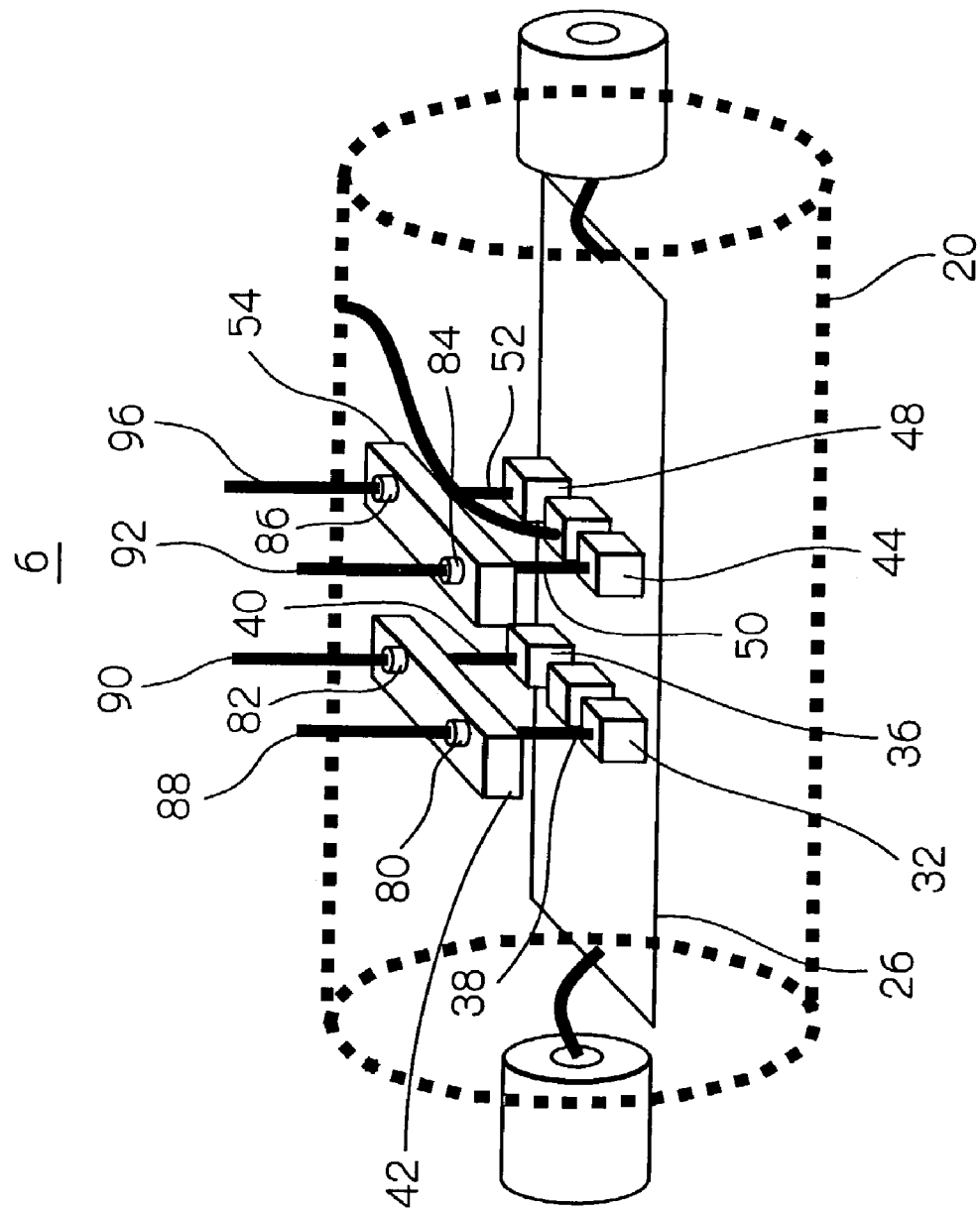
FIG. 7 is a schematic view showing a fourth embodiment of an optical sensor unit in accordance with the present invention.

FIG. 7 shows a fourth, still further alternative embodiment of the optical sensor unit in accordance with the present invention. The same parts or components as those shown in FIG. 1 are denoted with the same reference numerals. In FIG. 7, optical connectors for connecting inner optical fibers to outer optical fibers are mounted on the mounting base units 42 and 54 adapted for holding the optical fibers, such that the optical sensor unit 6 and external devices, such as the light source 5 or the photosensitive device 7, FIG. 2, will be interconnected using polarization plane holding optical fibers 88, 90, 92 and 96 liable to changes in the plane of polarization due to bending only to a smaller extent.

Specifically, an optical connector 80 connected to one end of the optical fiber 38 and an optical connector 82 connected to one end of the optical fiber 40 are mounted to the optical fiber mounting base unit 42, whilst an optical connector 84 connected to one end of the optical fiber 50 and an optical connector 86 connected to one end of the optical fiber 52 are mounted to the optical fiber mounting base unit 54. By introducing the optical connectors, connected to the ends of the optical fibers 88, 92, 90 and 96, connecting to the light source 5 or to the photosensitive device 7, FIG. 2, into the aforementioned optical connectors 80, 84, 82 and 86, the optical fibers 88, 90, 92 and 96 may be connected to the optical fibers 38, 50, 40 and 52, within the optical sensor unit 6, respectively.

In this case, it is a frequent occurrence that an external bending force is applied to the optical fibers 88, 92, 90 and 96, connecting the light source 5 and the photosensitive device 7. In the present embodiment of the optical sensor unit, since the optional optical fibers may be connected via optical connectors 80 to 86, signal degradation due to bending may be diminished by employing polarization plane holding fibers at least as the optical fibers 88 and 92, thus enabling the variations in the measurement signals to be diminished.

Figure 8:
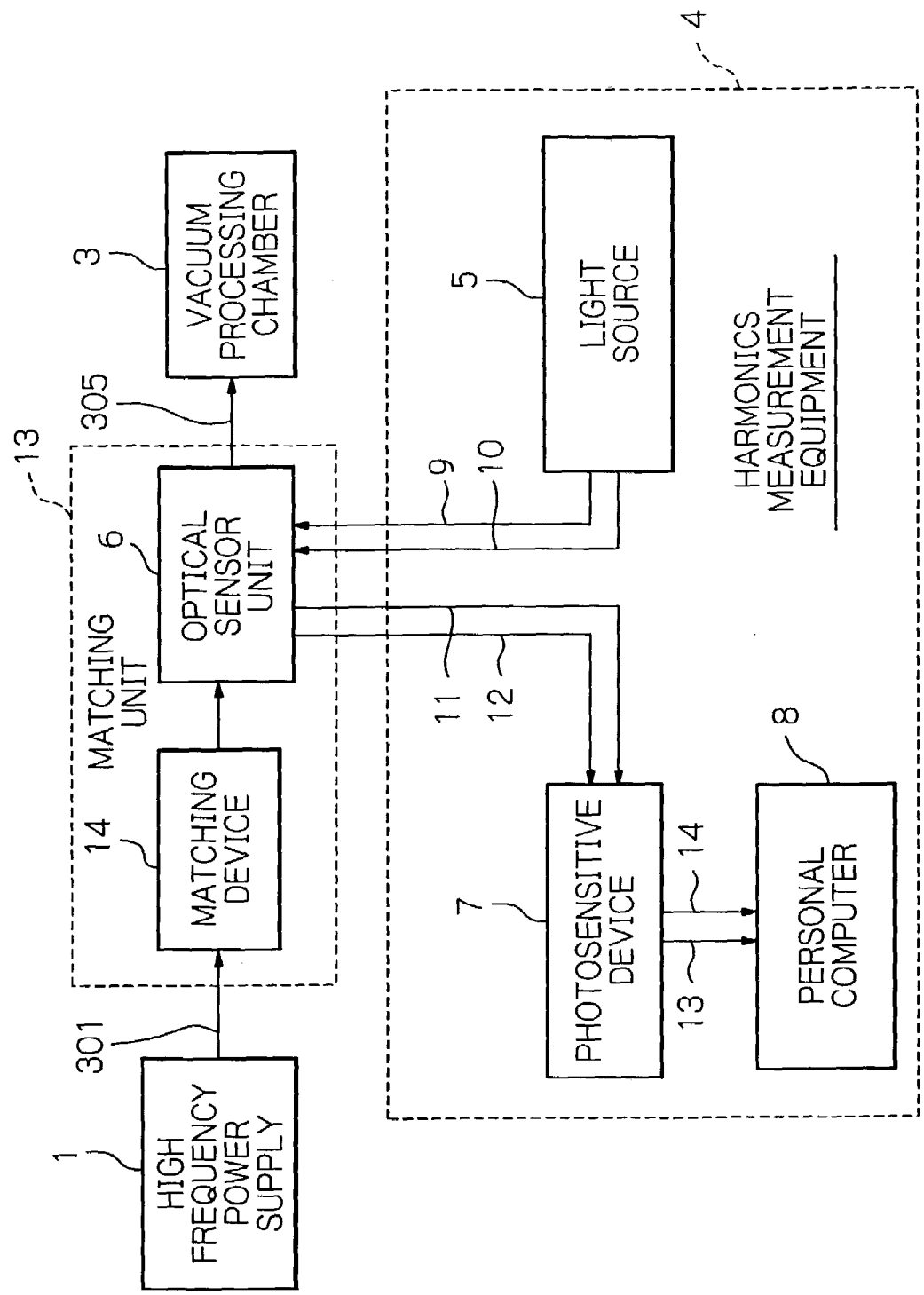
FIG. 8 is a schematic block diagram showing another embodiment of a semiconductor manufacturing system employing the harmonics measurement equipment including an optical sensor unit in accordance with the present invention.

FIG. 8 shows another embodiment of a semiconductor manufacturing system employing the harmonics measurement equipment including the optical sensor unit 6 in accordance with the present invention. In the semiconductor manufacturing system, shown in FIG. 2, the optical sensor unit 6 is introduced between the matching unit 2 and the vacuum processing chamber 3. In the present embodiment shown in FIG. 8, the optical sensor unit 6 is connected to the final stage on the output side within a matching unit 13 (the output side of a matching device 14), as understood from FIG. 8.

In the present embodiment shown in FIG. 8, in which the optical sensor unit 6 is mounted inside the matching device 13, measurement may be made even if there is no spacing sufficient to hold the optical sensor unit 6 between the matching device 13 and the vacuum processing chamber 3. Moreover, since the elongation of the high frequency transmission line caused by the introducing of the optical sensor unit 6 may be minimized, the effect of the transmission line on the system may be minimized.

Figure 9:
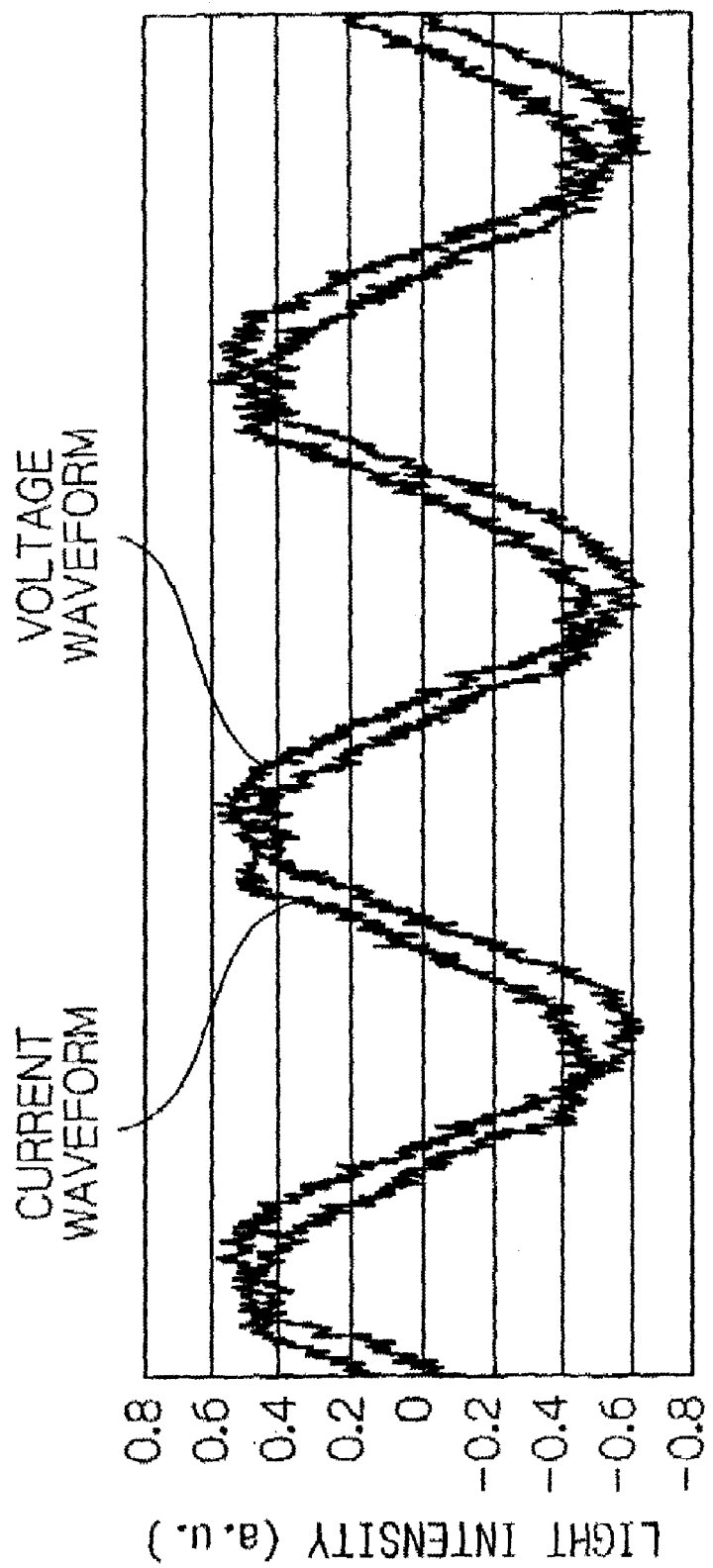
FIG. 9 plots waveforms of high frequency current and voltage as measured by an optical sensor unit in accordance with the present invention.

FIGS. 9 to 12 plot measured results in which the high frequency was measured using the optical sensor unit in accordance with the present invention. FIG. 9 shows the results of measurement of the high frequency current and voltage during the time of plasma discharge by the optical voltage and current sensors. The ordinate in the figure stands for the intensity of the light output from the optical sensor. The measurements are by a digital oscilloscope and not established by correlation with the actual current or voltage values. Thus, the measured results are indicated as light intensity. As may be seen from FIG. 9, optimum high frequency current and voltage waveforms may be obtained by employing the optical sensor unit according to the present embodiment for a semiconductor manufacturing system.

Figure 10:
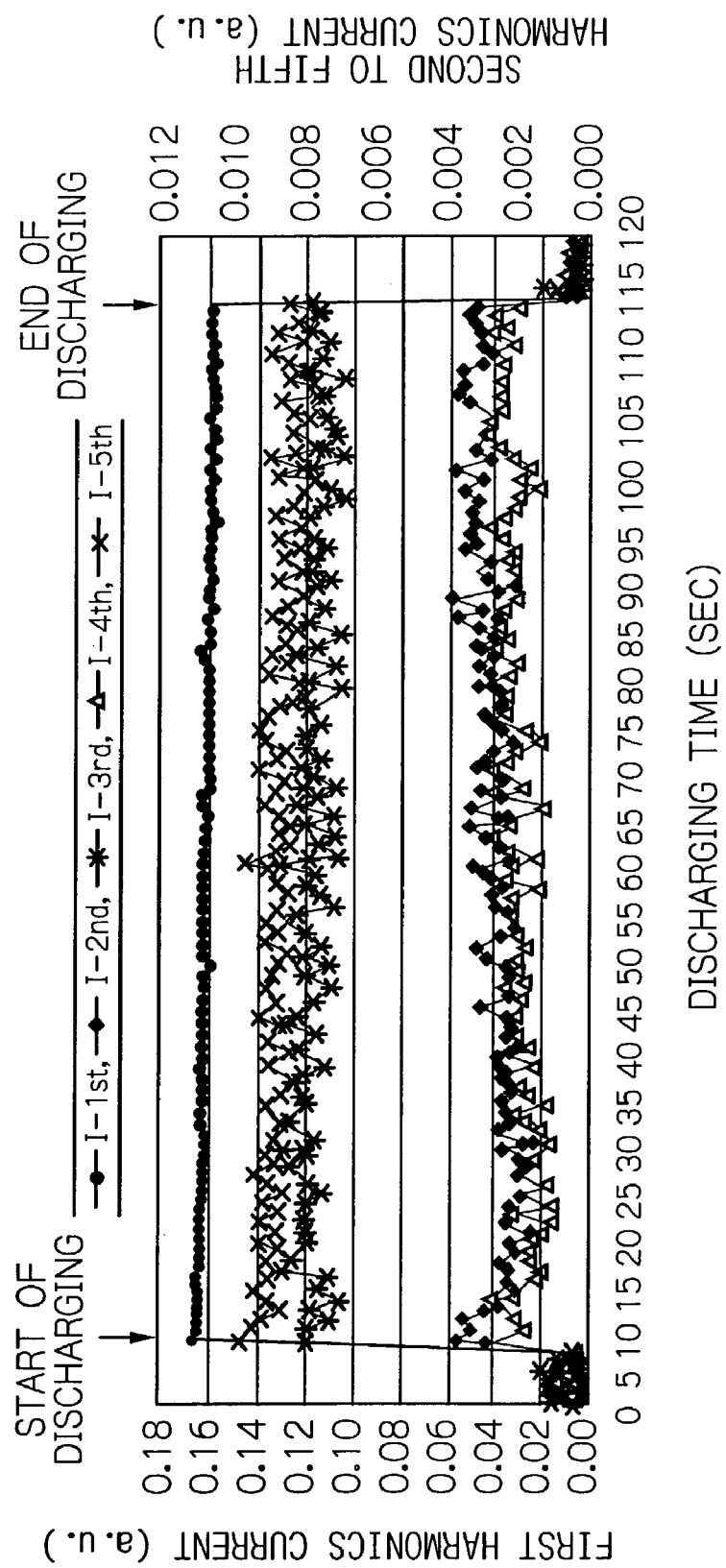
FIG. 10 plots harmonics currents obtained by analysis of the measured waveforms of FIG. 9 by the harmonics measurement equipment in accordance with the present invention.
Figure 11:
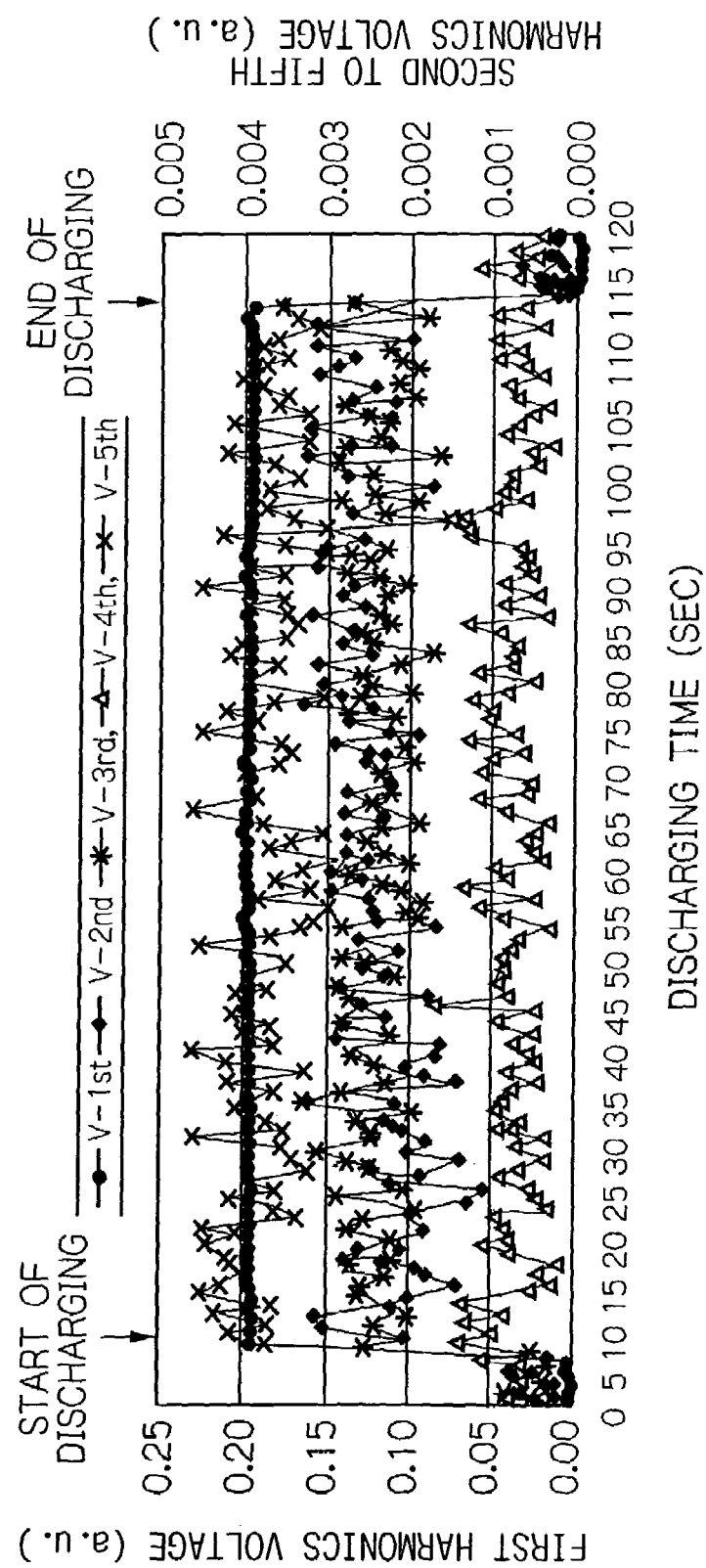
FIG. 11 plots harmonics voltages obtained by analysis of the measured waveforms of FIG. 9 by the harmonics measurement equipment in accordance with the present invention.
Figure 12:
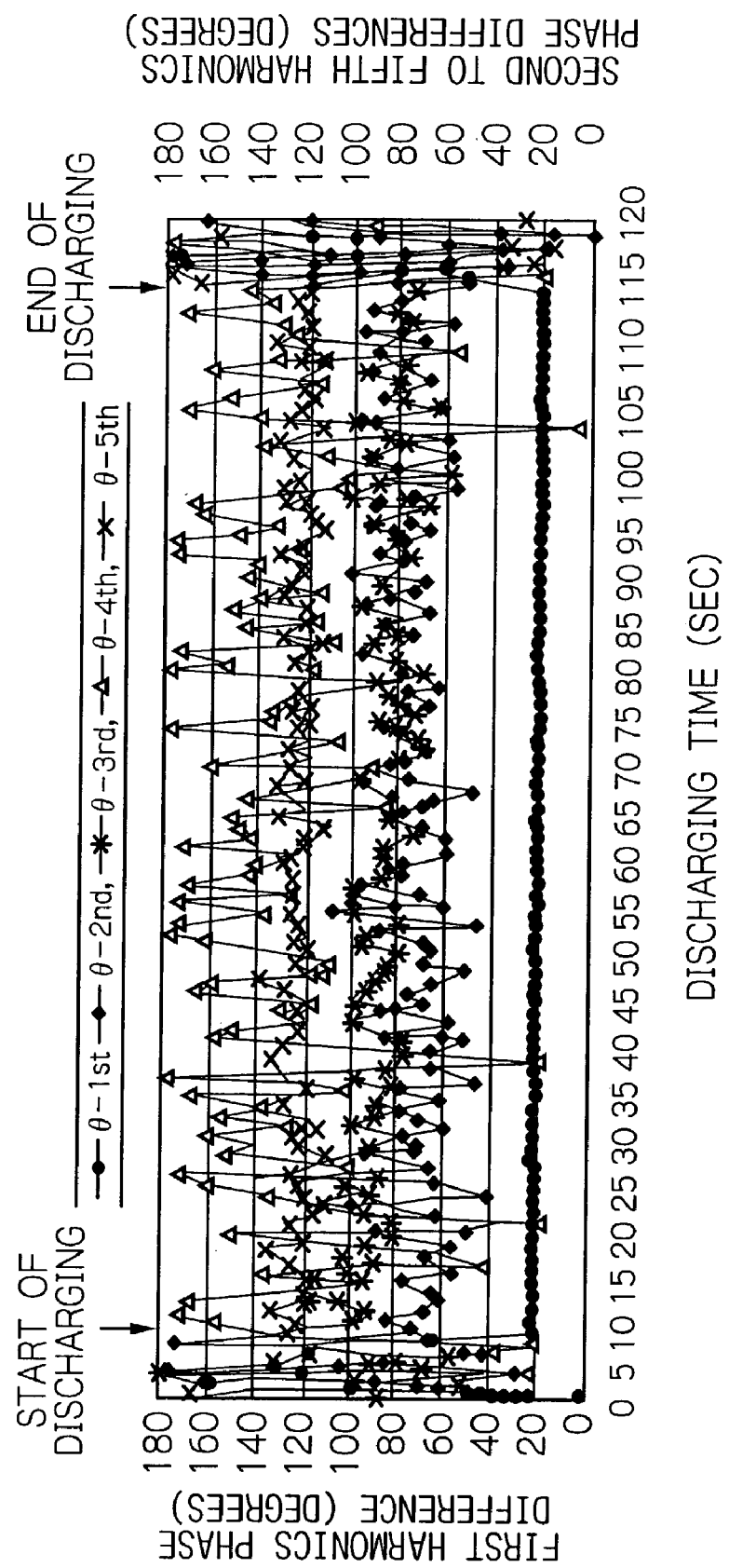
FIG. 12 plots harmonics phase differences obtained by analysis of the measured waveforms of FIG. 9 by the harmonics measurement equipment in accordance with the present invention.

FIGS. 10 to 12 show the results of fast Fourier transform of the current and voltage waveforms into respective harmonics components. Specifically, FIGS. 10, 11 and 12 respectively show the harmonics currents, voltages and phase differences. The ordinates of FIGS. 10 and 11 stand for the light intensity of the respective harmonics components. The ordinates of FIG. 12 stand for the phase difference in angular degrees. The abscissas of FIGS. 10 to 12 stand for the discharging time in seconds. The waveforms were measured every second, although this time interval may be set arbitrarily. The component values resulting from the FFT analysis are plotted in the form of graphs.

The entire disclosure of Japanese patent application No. 2002-252902 filed on Aug. 30, 2002, including the specification, claims, accompanying drawings and abstract of the disclosure is incorporated herein by reference in its entirety.

While the present invention has been described with reference to the particular illustrative embodiments, it is not to be restricted by the embodiments. It is to be appreciated that those skilled in the art can change or modify the embodiments without departing from the scope and spirit of the present invention.

What is claimed is:

1. An optical sensor unit comprising:
   a transmission line for propagating a high frequency;
   a current sensor unit for converting first incident light into a first optical signal, intensity of which varies in response to a magnetic field of the high frequency;
   a voltage sensor unit for converting second incident light into a second optical signal, intensity of which varies in response to an electric field of the high frequency;
   an optical input unit for introducing from light provided from outside the first incident light to said current sensor unit and the second incident light to said voltage sensor unit.

2. The optical sensor unit in accordance with claim 1, further comprising a first optical fiber for taking out the first optical signal to outside, and a second optical fiber for taking out the second optical signal to outside;
   said optical input unit comprising a third optical fiber for providing the light provided from outside to said current sensor unit, and a fourth optical fiber for providing the light from outside to said voltage sensor unit.

3. The optical sensor unit in accordance with claim 2, wherein said optical input unit further comprises an optical fiber type of optical coupler splitting the light provided from outside into the first and the second incident light, said optical coupler having an output side forming said third and fourth optical fibers.

4. The optical sensor unit in accordance with claim 2, wherein said third and fourth optical fibers are polarization plane holding fibers.

5. The optical sensor unit in accordance with claim 1, wherein said current sensor unit includes:
   a polarizer for linearly polarizing the first incident light to output linearly polarized light;
   a Faraday cell for rotating a plane of polarization of the linearly polarized light in response to the magnetic field of the high frequency; and
   an analyzer for converting light output from said Faraday cell into the optical signal, intensity of which varies according to the rotation of the plane of polarization of the light output from said Faraday cell.

6. The optical sensor unit in accordance with claim 1, wherein said voltage sensor unit includes:
   a polarizer for linearly polarizing the second incident light to output linearly polarized light;
   a Pockels cell for elliptically polarizing the linearly polarized light to output elliptically polarized light in response to the electric field of said high frequency;
   a quarter-wavelength plate for controlling polarization of the elliptically polarized light to output, when field strength within said Pockels cell is zero, circular polarized light; and
   an analyzer for converting the light output from said quarter-wavelength plate into an optical signal, intensity of which varies according to polarization of the linearly polarized light.

7. The optical sensor unit in accordance with claim 1, wherein said transmission line includes an electrically conductive sensor case, and a plate-like, electrical conductor held in said sensor case and electrically insulated from said sensor case,
   said conductor having a primary surface securing thereon said current sensor unit and said voltage sensor unit,
   said voltage sensor unit having a primary surface on which a first electrode is provided to be connected to said sensor case.

8. The optical sensor unit in accordance with claim 1, wherein said transmission line includes an electrically conductive sensor case, and a plate-like, electrical conductor held in said sensor case and electrically insulated from said sensor case, said conductor having a primary surface securing thereon said current sensor unit, said voltage sensor unit being secured at a distance from said conductor, said voltage sensor unit having one side surface receiving incident light and another side surface discharging the incident light, either of the side surfaces having a second electrode provided to be connected to said conductor, remaining one of the side surfaces having a third electrode provided to be connected to said sensor case.

9. The optical sensor unit in accordance with claim 8, wherein said second and third electrodes are optically transparent electrodes transmitting the light.

10. Harmonics measuring equipment comprising:
a light source for generating laser light;
an optical sensor unit including a current sensor unit for changing a plane of polarization of the laser light in response to a magnetic field of high frequency input from outside to generate a first optical signal, intensity of which varies in response to the magnetic field, and a voltage sensor unit for changing a plane of polarization of the laser light in response to an electric field of the high frequency to generate a second optical signal, intensity of which varies in response to the electric field;
a photosensitive device for converting the first and second optical signals into electrical signals; and
a data processor for analyzing the electrical signals to calculate harmonics components of the high frequency.

11. The equipment in accordance with claim 10, further comprising a polarization plane holding fiber interconnecting said optical sensor unit to said light source.

* * * * *